United States Patent [19]

Preston et al.

[11] 4,186,271
[45] Jan. 29, 1980

[54] UNSATURATED POLYOLS CONTAINING ALKENYL ARYL CONSTITUENTS

[75] Inventors: Frank J. Preston, Meriden; Kiran B. Chandalia, Hamden, both of Conn.

[73] Assignee: Olin Corporation, New Haven, Conn.

[21] Appl. No.: 942,220

[22] Filed: Sep. 14, 1978

Related U.S. Application Data

[63] Continuation of Ser. No. 783,355, Mar. 31, 1977, abandoned.

[51] Int. Cl.$^2$ ............................................. C07C 43/20
[52] U.S. Cl. ................................... 568/607; 560/104; 526/303; 526/295; 526/329.6; 526/334
[58] Field of Search ................ 568/607; 560/104, 112

[56] References Cited

U.S. PATENT DOCUMENTS

| 3,041,319 | 6/1962 | Abramo | 568/662 |
| 3,100,804 | 8/1963 | Abramo | 568/607 |
| 3,190,925 | 6/1965 | Stowe | 568/635 |

*Primary Examiner*—Bernard Helfin
*Attorney, Agent, or Firm*—Robert J. Feltovic; Thomas P. O'Day

[57] ABSTRACT

Unsaturated polyol compounds containing alkenyl aryl constituents are described. These unsaturated polyols are prepared by reacting a polyol with an aromatic derivative including both an alkenyl constituent and a second functionality reactive with a polyol. The resulting unsaturated polyols feature an alkenyl aryl constituent which enhances polyol receptivity for graft copolymerization with vinyl monomers. The aryl constituent along with multiple hydroxyl groups of the polyol render these polyols particularly suitable for polyurethane end uses.

5 Claims, No Drawings

UNSATURATED POLYOLS CONTAINING ALKENYL ARYL CONSTITUENTS

This is a continuation of application Ser. No. 783,355, filed Mar. 31, 1977, now abandoned.

BACKGROUND OF THE INVENTION

A. Field of the Invention

The invention relates to ethylenically unsaturated polyol compounds. In particular, the invention relates to alkenyl aryl polyols of the formula:

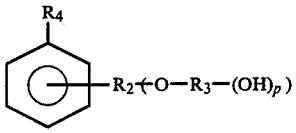

wherein
$R_4$ is straight or branched alkenyl of 2–10 carbons;
$R_2$ is lower alkyl of 1–4 carbons; or

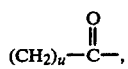

wherein u is an integer from 0–3;
p is an integer from 2–5; and
$(\text{—O—}R_3\text{—(OH)}_p)$ is a residue of a polyol, $R_3(\text{OH})_{p+1}$, with an equivalent weight ranging from about 250 to 5000, after removal of one hydroxy hydrogen therefrom.

B. Prior Art

Vinyl benzyl hydroxy alkyl ethers are known in the art, as exemplified by U.S. Pat. No. 3,079,369 to Abramo. The polymers described in this patent feature the monomer units:

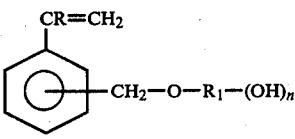

wherein
R is selected from the class consisting of hydrogen and methyl radical;
$R_1$ is a saturated alkyl radical of 2–10 carbons; and
n represents an integer of 1–2.

However, this patent is directed to compounds including only an alkyl hydroxy constituent which is dissimilar to the polyol constituent of the present invention. These vinyl benzyl hydroxy alkyl ethers lack the molecular weight and the polymeric linkages which are characteristic of the invented alkenyl aryl polyols.

Monomeric alkenyl benzyl polyglycol ethers also are known. For example, U.S. Pat. No. 3,190,925 to Stowe illustrates monomers such as:

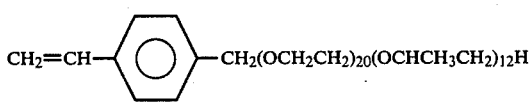

However, while this patent shows a vinyl benzyl ether, it does not describe the unsaturated polyols of the present invention which contain both a polyol chain with multiple hydroxyl groups and an alkenyl aryl constituent.

In order to improve polyurethane characteristics such as resilience and load bearing in foams, much art has been developed directed to incorporating higher molecular weight resinous materials into polyurethane formulations (e.g., U.S. Pat. No. 3,383,351 to Stamberger). One such method to accomplish this is to prepare and use graft copolymers of ethylenically unsaturated monomers and unsaturated polyols as exemplified by U.S. Pat. No. 3,966,521 to Patton et al. These graft copolymers are formed by polymerizing an unsaturated monomer, such as acrylonitrile, with an unsaturated polyol obtained by reacting an organic compound having both ethylenic unsaturation and a hydroxyl, carboxyl, or epoxy group with a polyol, or by reacting a sodium or potassium salt of a polyol with alkyl chloride or vinyl chloride.

Neither of these patents, however, describes the preparation or use of the unsaturated polyols of the present invention which features an alkenyl aryl constituent which enhances the polyol compatability in graft copolymerization with unsaturated monomers and offers physical property advantages in polyurethane end uses.

SUMMARY OF THE INVENTION

Now, novel unsaturated polyols have been developed. The alkenyl aryl polyols are prepared by the reaction of a polyol with an aromatic derivative containing both an alkenyl constituent and a second functionality reactive with a polyol. Because of the presence of the alkenyl aryl constituent on the resulting unsaturated polyol, the reactive compatability of the polyol with vinyl monomers is enhanced and hence stable graft copolymers of these unsaturated polyols with vinyl monomers are readily effected. The alkenyl aryl polyols feature multiple hydroxyl groups which make them particularly suited for end use in polyurethane applications.

DETAILED DESCRIPTION OF THE PREFERRED EMBODIMENTS

The alkenyl aryl polyols of the present invention can be represented by the general formula:

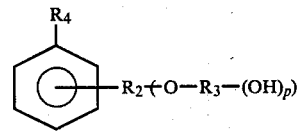

I wherein
$R_4$ is straight or branched alkenyl of 2–10 carbons;
$R_2$ is lower alkyl of 1–4 carbons; or

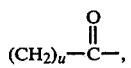

wherein u is an integer from 0–3;
p is an integer from 2–5; and
$(\text{—O—}R_3\text{—(OH)}_p)$ is a residue of a polyol, $R_3(\text{OH})_{p+1}$, after removal of one hydroxy hydrogen therefrom.

These alkenyl aryl polyols can be prepared by reacting a polyol with an alkenyl aryl reactant which contains a second functionality reactive with a polyol. This second reactive functionality may be such as an alkyl halide, a carboxylic acid or acid halide group or an ester. These functionalities are reactive with a hydroxyl group of a polyol so that the alkenyl aryl group can be incorporated onto the polyol chain.

The alkenyl aryl reactant can be represented by the general formula:

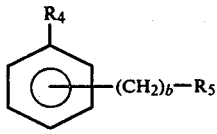
II wherein
R$_4$ is straight or branched alkenyl of 2–10 carbons;
b is an integer from 0–3; and
R$_5$ is a methyl halide group, a carboxylic acid group, corresponding carboxylic acid halides, or corresponding carboxylic acid lower alkyl esters of 1–4 carbons.

The alkenyl aryl reactants which can be used as to form the alkenyl aryl polyols include alkenyl aryl carboxylic acids such as alkenyl benzoic acids, alkenyl phenyl acetic acids, alkenyl phenyl propionic acids, alkenyl phenyl butyric acids, and the like, and their functional derivatives such as their acid halides and esters, which can readily be prepared from the acids by conventional means. Other alkenyl aryl compounds which can be used include alkenyl aryl alkyl halides such as alkenyl benzyl halides, alkenyl phenyl ethyl halides, alkenyl phenyl propyl halides, alkenyl phenyl butyl halides, and the like. The alkenyl segment of these compounds includes straight or branched chain alkenyl, such as ethenyl (e.g., for styryl), isopropenyl, propenyl (e.g., for allyl phenyl), butenyl, octenyl, decenyl, and the like. Polyethylenic alkenyl groups (dienes, trienes, etc.) also are included, such as butadienyl, pentadienyl, hexatriene, heptatrienyl, and the like.

Preferred are alkenyl aryl reactants of the formula:

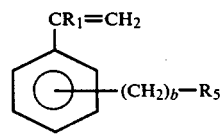
III wherein
R$_1$ is hydrogen or methyl and
b and R$_5$ are as defined in Formula II above.

Vinyl aryl alkyl halide, in specific, chloromethyl styrene, is particularly preferred. The chloromethyl styrenes can be prepared by various known methods, such as described in U.S. Pat. No. 3,049,503, column 2, lines 55–67.

The relative position of the second reactive functionality on the benzene ring of the alkenyl aryl compound is not critical to the invention. The preferred chloromethyl styrenes prepared by known methods commonly are ortho and para mixtures. It is further noted that one or more other constituents which are innocuous to the reaction, such as lower alkyl or halo constituents, may also be present at the open positions of the aromatic ring.

For purposes of simplicity in presentation, the preferred vinyl benzyl polyols have been chosen for discussion in further detail below. They can be prepared by a method exemplified by the following illustration:

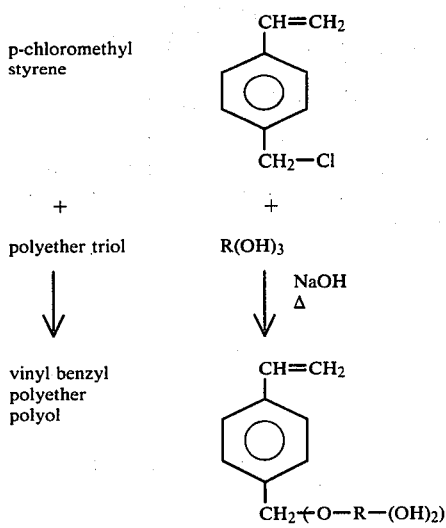

As depicted above, a vinyl alkenyl aryl compound having a second reactive functional alkyl halide group is reacted with a polyether triol in the presence of a base in a Williamson-type ether-forming synthesis. A molar ratio of polyol to alkenyl aryl compound of from 1:1 to 5:1 is preferred. A ratio of about 1.5 to 2.5:1 is particularly preferred. Any unreacted alkenyl aryl compound or polyol can be removed from the product by conventional means. However, for graft copolymer and polyurethane end use, it is preferred to use excess polyol reactant and then allow any excess unreacted polyol to remain with the alkenyl aryl polyol product. It has been found that this ether-forming reaction takes place in the presence of a base, such as sodium hydroxide, at a temperature range of from about 50° to 150° C., preferably from about 90° to 110° C. The base preferably should be used in about a 1–1.5:1 molar ratio with the alkenyl aryl alkyl halide. About a 1–1.2:1 ratio is most preferred. Sodium hydroxide reacts with a polyol hydroxy group to form a sodium alkoxide. The alkenyl aryl alkyl halide reacts with the sodium alkoxide, such that the alkoxide ion is substituted for the halide ion to result in the formation of the vinyl benzyl polyol ether, with sodium chloride forming as a by-product. The reaction involved proceeds in a manner similar to that between benzyl chloride and simple alcohols, as discussed in U.S. Pat. No. 3,190,925, column 2, lines 61–70. Any excess NaOH and the NaCl by-product can be removed by common clean-up procedures such as clay treatment and filtering.

When the second reactive functionality of the alkenyl aryl monomer is a carboxylic acid, acid chloride or ester group, the reaction with the polyol is an esterification or a transesterification-type reaction, proceeding in common fashion, in non-basic media.

The polyol reactant which is used in preparing the alkenyl aryl polyols of the invention can be any such compound, including mixtures of two or more such compounds, having 3–6 hydroxyl groups and preferably an average equivalent weight from about 250 to about 5000. This includes polyester polyols and polyether polyols. However, the polyether polyols are generally preferred.

The polyester polyols include the products of reacting polycarboxylic acids with polyhydric alcohols. Illustrative polycarboxylic acids include, for example, oxalic, malonic, succinic, glutaric, adipic, pimelic, suberic and azelaic acids and the like. Illustrative polyhydric alcohols include various triols, tetrols and higher-functionality alcohols, such as glycerol, trimethylolpropane, pentaerythritol, sorbitol, mixtures thereof and the like.

The polyether polyols, the use of which is preferred herein, include various polyoxyalkylene polyols and mixtures thereof. These can be prepared, according to well-known methods, by condensing an alkylene oxide, or a mixture of alkylene oxides using random or step-wise addition, with a polyhydric initiator or mixture of initiators. Illustrative alkylene oxides include ethylene oxide, propylene oxide, butylene oxide and the halogenated alkylene oxides such as trichlorobutylene oxide and so forth. The most preferred alkylene oxide is propylene oxide or a mixture thereof with ethylene oxide using random or step-wise oxyalkylation.

The polyhydric initiators used in preparing the polyether polyol reactant can be any such material which has from 3 to 6 active hydrogens. This includes (a) the aliphatic triols such as glycerol, trimethylolpropane, triethylolpropane, trimethylolhexane and the like, (b) higher-functionality alcohols such as sorbitol, pentaerythritol, methyl glucoside and the like, (c) the polyamines such as tetraethylene diamine and (d) the alkanolamines such as diethanolamine, triethanolamine and the like.

A preferred group of polyhydric initiators for use in preparing the polyether polyol reactant is one which comprises aliphatic triols such as glycerol, trimethylolpropane and the like.

The alkylene oxide-polyhydric initiator condensation reaction is preferably carried out in the presence of a catalyst such as KOH as is well known in the art. In effecting the reaction, a sufficient proportion of alkylene oxide is used as to provide a final polyol product having an average equivalent weight of about 250–5000, preferably about 700–3000 and more preferably about 1000–1500. The catalyst is thereafter preferably removed, leaving a polyether polyol which is ready for use in preparing the alkenyl aryl polyols of the invention.

The alkenyl aryl polyols of the present invention are useful in forming graft copolymers. The alkenyl aryl polyols are treated with an ethylenically unsaturated monomer, or a mixture of such monomers, usually in the presence of additional polyol, selected from the polyols as defined above. The monomers useful in the copolymerization process are any polymerizable monomers characterized by the presence of at least one polymerizable ethylenic unsaturated group of the type $>C=C<$. Such monomers are exemplified by those described in U.S. Pat. No. 3,383,351, column 4, lines 61–75 and column 5, lines 1–40.

Preferred monomers include styrene, acrylonitrile, vinyl chloride, methyl methacrylate, hydroxy ethyl acrylate, butadiene, isoprene, chloroprene, and the like. In particular, styrene and acrylonitrile have been found to be preferred.

During the free radical grafting polymerization, any suitable free radical initiator may be used such as hydrogen peroxide, organic peroxides, such as benzoyl peroxide, dicumyl peroxide, cumene hydroperoxide, etc. Any azo initiator also is suitable, such as azo-bis isobutyronitrile, 4,4'-azo-bis-(4-cyanopentanoic acid), and the like. Azo-bis isobutyronitrile (ABIN) has been found to be preferable.

The over-all grafting reaction can be characterized by the following example:

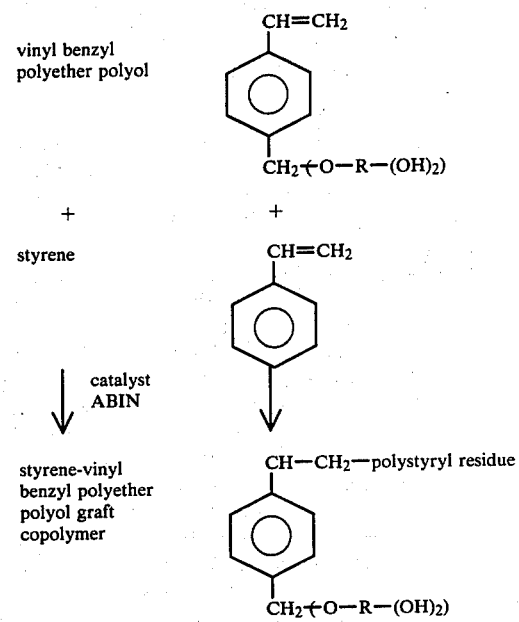

The graft copolymers formed are particularly suited for use in polyurethane formulations. Presence of multiple terminal hydroxyl groups allows for reaction with polyisocyanates. Arrangements modifying the amount of terminal hydroxyls result in variation of the extent of branching and cross-linking in the resulting polyurethanes. Such variations offer applicability to a wide range of polyurethane uses including elastic fibers, elastomers, or flexible, semi-rigid, or rigid foams.

In particular, in the area of polyurethane foam applications, the incorporation of aromatic constituents on the polyol chain serves to enhance desirable properties such as resilience and load bearing. Further, the presence of the alkenyl aryl constituent on the polyol increases the reactive compatability of the unsaturated polyol with vinyl monomers.

The following examples are provided to further illustrate the invention. All parts and percentages are by weight unless otherwise specified.

Preparation of Alkenyl Aryl Polyols

EXAMPLE I

Preparation of Vinyl Benzyl Polyol Ether 3 g (0.075 moles) NaOH was added to 325 g (0.072 moles) of a polyether triol made from glycerin by block addition of propylene oxide capped by ethylene oxide to form a polyether triol having >70% primary hydroxyl groups and an average molecular weight of about 4500. The mixture was stirred under N$_2$ at 90° to 100° C. for two hours, until all the NaOH dissolved. 6 g (0.04 moles) of chloromethyl styrene was then added and the reaction was allowed to continue for two hours at 90° C. The product was then treated with 16 g supercel and 16 g magnesol to remove the salt and any unreacted NaOH, filtered through Whatman No. 1 filter paper, and then stripped at 2 mm Hg at 100° C. for one hour to remove any unreacted chloromethyl styrene reactant.

UV and IR analyses indicated the presence of vinyl and benzene moieties to confirm formation of the vinyl benzyl polyol ether product. The OH number was analyzed to be 31.7 mg KOH/g. This is in good agreement with the theoretical OH number of 31.0 mg KOH/g for the anticipated vinyl benzyl polyol ether product.

EXAMPLE II

Preparation of Vinyl Benzyl Polyol Ether

A 3-liter, three-neck flask equipped with $N_2$ inlet, thermometer, feed inlet and stirrer was charged with 1500 g (0.332 moles) of a polyether triol made from glycerol by block addition of propylene oxide capped with ethylene oxide to form a polyether triol having about 4500 molecular weight containing 10 percent EO as end block. To this was added about 28 g of a 50 percent solution of sodium hydroxide in water. The mixture was purged with $N_2$ under surface for 20 minutes. The flask was then heated to 110° C. for two hours. The water then was purged out with $N_2$ and the reactor was cooled to 50° C. 27.7 g (0.185 moles) of vinyl benzyl chloride was then added dropwise. The reaction was allowed to continue for four and one-half hours. The contents showed the formation of a white solid (likely to be NaCl, a by-product of reaction).

The salt and any unreacted NaOH were removed by clay treatment. 30 g microcell, 30 g magnesol and 15 g celite were added to the flask and mixed at 110° C. for two hours. The material was then filtered hot through Whatman No. 1. filter paper with <5 mm Hg pressure. A yellow, clear product was obtained, which was stripped to remove unreacted vinyl benzyl chloride. UV indicated the presence of a benzene ring and unsaturation moieties to confirm formation of the vinyl benzyl polyol ether product. This material had a hydroxyl number of 33.8 mg KOH/g and unsaturation equal to 0.15 milliequivalent/g.

Preparation of Graft Copolymers

EXAMPLE III

The product of Example I was used to make a graft copolymer with styrene by free radical reaction.

15 g of the product of Example I was mixed with 5 g styrene and 0.4 g ABIN (azo-bis-isobutyronitrile). The mixture was stirred at 80°–95° C. for one hour. The viscosity of the product was 6400 cps. NMR analysis for aliphatic and aromatic protons showed that the product contained 23 percent styrene. Gel Permeation Chromatography molecular weight analysis confirmed copolymer formation.

EXAMPLE IV

The product of Example I was used to make a graft copolymer with styrene and acrylonitrile by free radical reaction.

24 g of the product of Example I was added to 16 g of the polyol reactant used in Example I and this was stirred and heated, under $N_2$, at 100° C. to form a uniform blend. To this was added a mixture of 4.5 g styrene, 0.5 g acrylonitrile and 0.15 g ABIN, and allowed to react for one hour at 80°–95° C. The product was then stripped to remove any unreacted monomers. The viscosity of the product was found to be 1500 cps at 25° C. (about 700 units more than the starting polyol reactant). The graft copolymer product was determined to contain about 11 percent polyethylenic residues. Gel Permeation Chromatography confirmed copolymer formation. The copolymer product was yellow, but non-turbid.

EXAMPLE V

The vinyl benzyl polyol (product of Example II) was used to make a copolymer with styrene as follows:

A 1-liter, three-neck flask equipped with $N_2$ inlet, feed inlet, stirrer, thermometer and reflux condenser was charged with 222 g of the polyether triol reactant used in Example II. The flask was heated under a $N_2$ blanket to 100° C. A "blend" of 1.7 g azo-bis isobutyronitrile, 6 g acrylonitrile, 50 g styrene and 222 g of the alkenyl aryl polyol product material from Example II was made. When the flask reached 100° C., the above-described blend was fed to the flask at a steady rate of 1.4 g/min. The feed time was three hours and twenty minutes. At the end of feeding operation, the reaction was then allowed to continue for one hour. The material was then stripped at 100° C. and <5 mm Hg vacuum to remove any unreacted monomer. The material balance at the end showed that 96 percent of the monomers charged reacted to form graft copolymer.

The final product had a viscosity of 4750 cps (at 25° C.), hydroxyl number of 33.1 mg KOH/g. The material is slightly yellow in color and translucent.

We claim:

1. An ethylenically unsaturated alkenyl aryl polyol characterized by the formula:

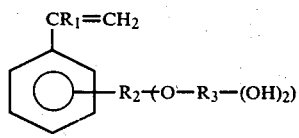

wherein
$R_1$ is hydrogen or methyl;
$R_2$ represents a lower alkylene radical of 1–4 carbons; and
—O—$R_3$—$(OH)_2$) represents a residue of a polyether polyol, $R_3(OH)_3$, wherein $R_3$ represents a polyether chain, with an equivalent weight ranging from 1000 to 1500, after removal of one hydroxy hydrogen therefrom.

2. The unsaturated polyol of claim 1 wherein $R_2$ represents —$CH_2$—.

3. The unsaturated polyol of claim 1 wherein $R_1$ is hydrogen.

4. The unsaturated polyol of claim 1 wherein $R_3$ comprises a polyether chain derived from a single alkylene oxide or a mixture of alkylene oxides.

5. The unsaturated polyol of claim 4 wherein $R_3$ comprises a polyether chain derived from the group consisting of propylene oxide, ethylene oxide or mixtures thereof.

* * * * *